United States Patent [19]

Mohacsi et al.

[11] Patent Number: 4,640,930

[45] Date of Patent: Feb. 3, 1987

[54] NAPHTHO(1,8-BC)-1,5-THIAZOCINONES

[75] Inventors: Erno Mohacsi, Summit; Jay P. O'Brien, Cedar Grove, both of N.J.

[73] Assignee: Hoffmann-La Roche Inc., Nutley, N.J.

[21] Appl. No.: 843,317

[22] Filed: Mar. 24, 1986

[51] Int. Cl.$^4$ .................... A61K 31/55; C07D 281/18
[52] U.S. Cl. ...................................... 514/431; 540/456
[58] Field of Search .................. 260/239.3 T; 514/431

[56] References Cited

U.S. PATENT DOCUMENTS

| | | | |
|---|---|---|---|
| 3,155,649 | 11/1964 | Krapcho | 260/239.3 B |
| 3,562,257 | 2/1971 | Kugita et al. | 260/239.3 B |
| 4,438,035 | 3/1984 | Gaino et al. | 260/239.3 B |
| 4,490,292 | 12/1984 | Maki et al. | 260/239.3 B |
| 4,547,495 | 10/1985 | Maiorana et al. | 260/239.3 B |
| 4,566,995 | 1/1986 | Simonovitch et al. | 260/239.3 B |
| 4,567,175 | 1/1986 | Takeda et al. | 260/239.3 B |

OTHER PUBLICATIONS

Kugita et al., Chem. Pharm. Bull 18 (10) 2028–2037 (1970).
Kugita et al., Chem. Pharm. Bull. 19, 595–602 (1971).
Meshi et al., Chem. Pharm. Bull. 19(8), 1546–1556 (1971).
Sato et al., Arzneim-Forsch. (Drug. Res.) Jahrgant 21 Nr. 9 (1971), 1338–1342.
Inoue et al., Chem. Soc. Perkin Trans. I (1984), 1725–1732.
CA 71(15):70657j.
CA 77(1): 5554h.
CA 75(9): 63848b.
CA 75(5): 36165v.
CA 74(25): 141721a.
CA 78(19): 119419u.
CA 75(9): 61652j.
CA 97(18): 150634b.
CA 77(1): 105c.
CA 76(11): 59674v.
CA 76(15): 85854y.
CA 78(11): 66993t.
CA 93(21): 197787m.
CA 79(11): 66331w.
CA 87(19): 145450c.
CA 97(25): 208153n.
CA 83(7): 58901z.
CA 90(3): 23002z.
CA 90(17): 137874r.
CA 93(23): 215403y.
CA 97(21): 174401z.
CA 96(18): 149164w.
Inoue et al., Chem. Pharm. Bull 33(3), 1256–1259 (1985).
CA 73(13): 66641y.
Abstracts of GB 2154–557-A and 578-A.

Primary Examiner—Robert T. Bond
Attorney, Agent, or Firm—Jon S. Saxe; Bernard S. Leon; Matthew Boxer

[57] ABSTRACT

A compound of the formula

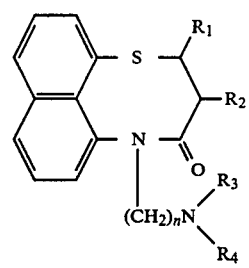

I wherein $R_1$ is phenyl substituted with 1 to 3 lower alkoxy groups, or 1 to 3 halogens; $R_2$ is hydroxy or lower alkanoyloxy; $R_3$ and $R_4$ are each independently lower alkyl or together form a pyrrolidine or piperidine ring; and n is 2 to 4, and pharmaceutically acceptable acid addition salts thereof are described. The compounds of formula I are active as calcium channel blockers and accordingly, are useful as agents for lowering blood pressure, and as agents for treating ischemia.

33 Claims, No Drawings

NAPHTHO(1,8-BC)-1,5-THIAZOCINONES

BRIEF SUMMARY OF THE INVENTION

The invention relates to compounds of the formula

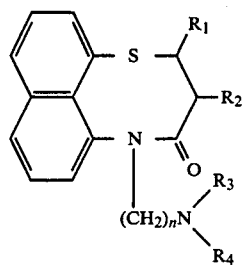

wherein $R_1$ is phenyl substituted with 1 to 3 lower alkoxy groups or 1 to 3 halogens; $R_2$ is hydroxy or lower alkanoyloxy; $R_3$ and $R_4$ are independently lower alkyl or together form a piperidine or pyrrolidine ring; and n is 2 to 4; and pharmaceutically acceptable acid addition salts thereof.

The compounds of formula I are active calcium channel blockers and accordingly are useful as agents for lowering blood pressure, and as agents for the treatment of ischemia.

DETAILED DESCRIPTION OF THE INVENTION

As used herein, the term "lower alkyl" denotes a straight or branched chain alkyl group containing 1 to 4 carbon atoms, for example, methyl, ethyl, propyl, isopropyl, butyl, and the like. The term "lower alkoxy" denotes a straight or branched chain lower alkoxy group containing 1 to 4 carbon atoms, for example, methoxy, ethoxy, propoxy, isopropoxy, butoxy, and the like. The term "halogen" denotes the halogens, that is, bromine, chlorine, fluorine and iodine. The term "lower alkanoyloxy" denotes a straight or branched chain alkanoyloxy group of 2 to 5 carbon atoms, for example, acetyloxy, propionyloxy, butyryloxy, isopropionyloxy, and the like.

The invention relates to compounds of the formula

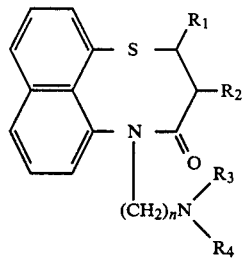

wherein $R_1$ is phenyl substituted with 1 to 3 lower alkoxy groups of 1 to 3 halogens; $R_2$ is hydroxy or lower alkanoyloxy; $R_3$ and $R_4$ are independently lower alkyl or together form a piperidine or pyrrolidine ring; and n is 2 to 4; and pharmaceutically acceptable acid addition salts thereof.

The compounds of formula I are active as calcium channel blockers and accordingly, are useful as agents for lowering blood pressure, and as agents for the treatment of ischemia.

As used in the formulas herein a solid line (━━━) indicates a substituent that is above the plane of the sulfur and nitrogen containing ring, a dotted line (⋯⋯⋯) indicates a substituent that is below the plane of the sulfur and nitrogen containing ring. The compounds of formula I contain two assymetric centers at the 2- and 3-positions. Accordingly, the compounds of formula I can be stereoisomers, that is, cis or trans isomers. As used herein, the term "cis" denotes a compound wherein the $R_1$ and $R_2$ substituents are both on the same side of the sulfur and nitrogen containing ring. As used herein, the term "(+)-cis" denotes an enantiomer having an absolute configuration analogous to that of (2S,3S)-3-(acetyloxy)-2,3-dihydro-5-[2-(dimethylamino)ethyl]-2-(4-methoxyphenyl) naphtho[1,8-bc]-1,5-thiazocin-4(5H)-one, which is a (+)-cis compound of the invention.

A compound of the formula

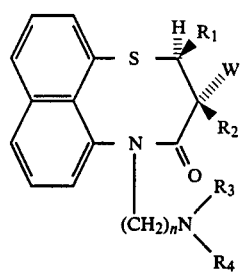

wherein $R_1$, $R_2$, $R_3$, $R_4$ and n are as described above is a (+)-cis compound of the invention.

A compound of the formula

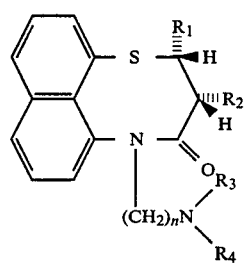

wherein $R_1$, $R_2$, $R_3$, $R_4$ and n are as described above is the enantiomer of a compound of formula $I^I$, and a (−)-cis compound of the invention.

Preferred compounds of the invention are cis compounds.

Especially preferred compounds of the invention are (+)-cis compounds.

As used herein the term "trans" denotes a compound wherein the $R_1$ and $R_2$ substituents are on opposite sides of the sulfur and nitrogen containing ring.

A compound of the formula

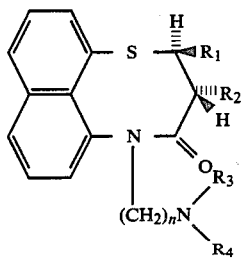

wherein $R_1$, $R_2$, $R_3$, $R_4$ and n are as described above is a trans compound of the invention.

A compound of the formula

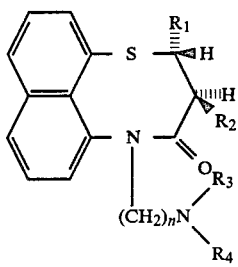

$I^{IV}$ wherein $R_1$, $R_2$, $R_3$, $R_4$ and n are as described above is the enantiomer of a compound of formula $I^{III}$, and another trans compound of the invention.

Preferred compounds of formula I are also those wherein $R_1$ is 4-alkoxyphenyl such as 4-ethoxyphenyl or more preferably 4-methoxyphenyl; $R_2$ is hydroxy or lower alkanoyloxy, such as propionyloxy or especially acetyloxy; and $R_3$ and $R_4$ are each ethyl or especially where $R_3$ and $R_4$ are each methyl; and n is 3 or preferably 2; enantiomers, diastereomers or racemates thereof; and pharmaceutically acceptable acid addition salts thereof. Of these, as has been described above, cis compounds are preferred and (+)-cis compounds are especially preferred.

Exemplary of compounds of formula I are:

(+)-cis-3-(Propionyloxy)-2,3-dihydro-5-[2-(dimethylamino) ethyl]-2-(4-methoxyphenyl)naphtho[1,8-bc]-1,5-thiazocin-4(5H)-one;

(±)-cis-3-(Acetyloxy)-2,3-dihydro-5-[2-(dimethylamino)ethyl]-2-(4-ethoxyphenyl)naphtho[1,8-bc]-1,5-thiazocin-4(5H)-one;

(±)-cis-2,3-Dihydro-5-[2-(dimethylamino)propyl]-3-hydroxy-2-(4-methoxyphenyl)naphtho[1,8-bc]-1,5-thiazocin-4(5H)-one;

(±)-cis-3-(Acetyloxy)-2,3-dihydro-5-[2-(diethylamino)ethyl]-2-(4-methoxyphenyl)naphtho[1,8-bc]-1,5-thiazocin-4(5H)-one;

(+)-cis-3-(Acetyloxy)-2,3-dihydro-5-[2-(methylethylamino)ethyl]-2-(4-methoxyphenyl)naphtho[1,8-bc]-1,5-thiazocin-4(5H)-one; and (+)-cis-3-(Butyryloxy)-2,3-dihydro-5-[2-(methylethylamino)ethyl]-2-(4-propoxyphenyl)naphtho[1,8-bc]-1,5-thiazocin-4(5H)-one.

A preferred compound of formula I is:

(±)-cis-2,3-Dihydro-5-[2-(dimethylamino)ethyl]-3-hydroxy-2-(4-methoxyphenyl)naphtho[1,8-bc]-1,5-thiazocin-4(5H)-one.

A most preferred compound of formula I is:

(+)-cis-3-(Acetyloxy)-2,3-dihydro-5-[2-(dimethylamino)ethyl]-2-(4-methoxyphenyl)naphtho[1,8-bc]-1,5-thiazocin-4(5H)-one.

The preparation of the compounds of formula I is exemplified as hereinafter described.

The compounds of formula Ia can be prepared as shown in Formula Scheme I below.

FORMULA SCHEME I

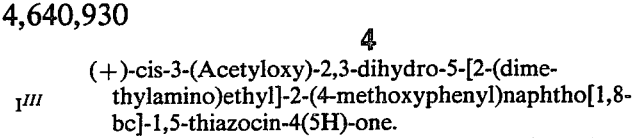

II     III     IV

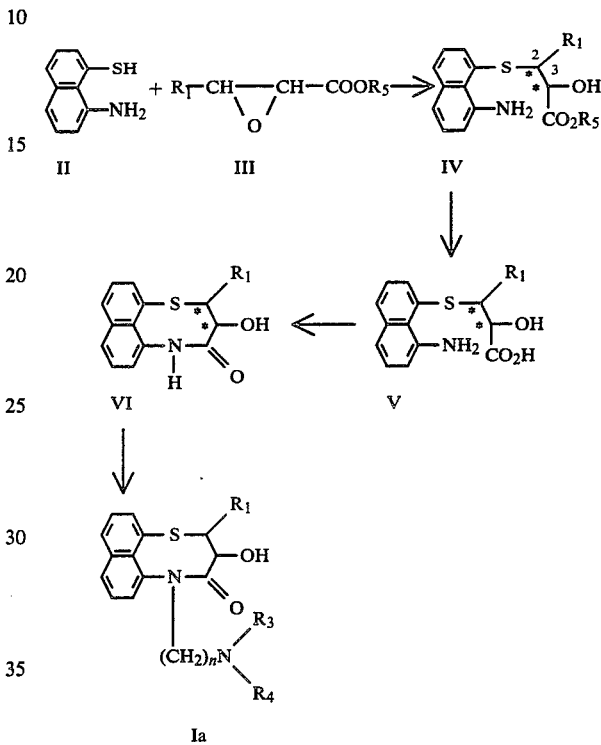

Ia wherein $R_1$, $R_3$, $R_4$, and n are as described above, *'s indicate assymetric carbons and $R^5$ is lower alkyl.

In connection with Formula Scheme I, 1,8-naphthosultam of formula II is reacted with a compound of the formula

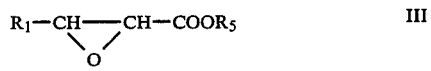

wherein $R_1$ and $R_5$ are as described above, to give a compound of the formula

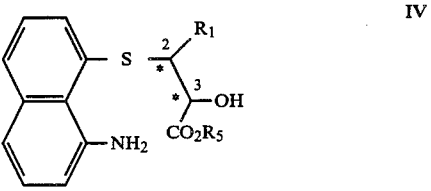

wherein $R_1$, $R_5$ and * are as described above.

This reaction is carried out without solvent or in the presence of an aromatic solvent, such as benzene, toluene, xylene or ethylbenzene at a temperature in the range of from about 100° to about 140° for about 1 to about 20 hours under an argon or more preferably nitrogen atmosphere. The molar ratio of the reactants is not critical. Preferably, the reactants are utilized in a 1:1 molar ratio. The product can be separated according to conventional means such as column chromatography. Compounds of formula IV have two asymmetric carbons at the 2- and 3-positions, as indicated by the *'s which appear in formula IV. Accordingly, the compounds of formula IV exist in two stereoisomeric forms, the erythro and threo-isomers.

The terms "erythro" and "threo" refer to the relative configurations of the hydroxy and phenyl groups substituted at the 2- and 3-positions of the compounds of formula IV and V. More specifically, the term "erythro" denotes compounds of formulas IV and V wherein the hydroxy and phenyl groups appear on the same side of the bond between the 2- and 3-positions in a Fischer's projection formula. The term "threo" denotes compounds of formula IV and V wherein the hydroxy and phenyl groups appear on the opposite sides of the bond between the 2- and 3-positions in a Fischer's projection formula. A Fischer's projection formula of an erythro compound of formula IV is depicted just below

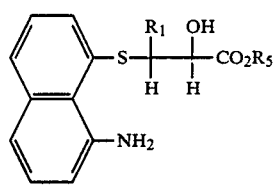

wherein $R_1$ and $R_5$ are as described above.

A Fischer's projection formula of a threo compound of formula IV is depicted just below

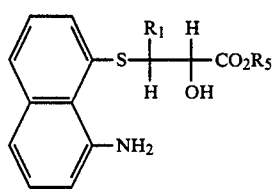

wherein $R_1$ and $R_5$ are as described above.

An erythro compound of formula IV or V is obtained as a racemate and further reacted as a racemate. A threo compound of formula IV or V is obtained as a racemate and further reacted as a racemate. Accordingly, when it is stated that a mixture of erythro and threo compounds has been obtained, it is meant that a mixture of the racemate of an erythro compound and a racemate of the threo compound have been obtained. When it is stated that an erythro compound is isolated, it is meant that the racemate of an erythro compound is isolated. When it is stated that a threo compound is isolated, it is meant that the racemate of a threo compound is isolated.

A mixture of erythro and threo compounds of formula IV are used in the next step, which appears in Formula Scheme I.

A compound of formula IV or a mixture of erythro and threo compounds of IV can be hydrolyzed to a compound of formula

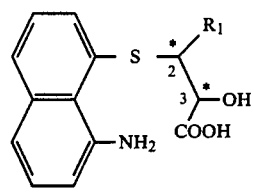

wherein $R_1$ is as described above, by conventional hydrolysis methods such as, for example, treatment with an inorganic acid such as, hydrochloric or sulfuric acid, or by treatment with an alkali base such as, potassium hydroxide, or more preferably sodium hydroxide.

The reaction is conducted in a polar organic solvent such as, propanol or more preferably ethanol at reflux for a period of about 10 minutes to about 1 hour. Separation of the products, which are a mixture of erythro and threo acids of formula V, wherein erythro and threo have the same definitions as described above, is carried out by successive recrystallizations with polar organic solvents. An especially preferable series of recrystallizations is a recrystallization first from methylene chloride, and then from acetonitrile to obtain a pure erythro compound of formula V. The threo compound of formula V, which would remain in the mother liquor of acetonitrile can be obtained by conventional means such as, evaporation of the acetonitrile, dissolution of the residue in ethyl acetate and extraction of the organic solution with strong inorganic acid such as, 1N hydrochloric acid, treatment of the acid solution with base and isolation of the threo compound by filtration.

An erythro compound formula V can be cyclized to a racemate of a compound of formula

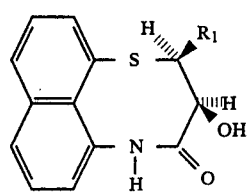

wherein $R_1$ is as described above, by reaction in the presence of a small amount of organic base such as, piperidine, or more preferably triethylamine in an aprotic, organic solvent such as, benzene, toluene, acetonitrile, or more preferably dimethylformamide, and further in the presence of a catalyst such as 2-iodo-1-methylpyridinium iodide.

The reaction is conducted at about room temperature for about 1 to about 20 hours, and separation can be by conventional means such as, crystallization. The cyclized compound of formula $VI^I$ is obtained in the form of a racemate.

A threo compound formula V can also be cyclized to a racemate of a compound of formula

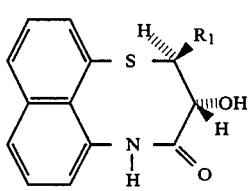

wherein $R_1$ is as described above, by heating in an organic aromatic solvent such as ethylbenzene, toluene or more preferably xylene. The reaction can be conducted at the refluxing temperature of the solvent employed and separation can be by conventional means such as, crystallization. The cyclized compound of formula $VI^{II}$ is obtained in the form of a racemate.

In the reactions described below, a compound of the formula

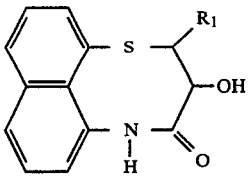

VI designates either a cis compound of formula $VI^I$ or a trans compound of formula $VI^{II}$.

Employing a compound of formula $VI^I$ in the reactions described below results in a cis compound of the invention. Employing a compound of formula $VI^{II}$ in the reactions described below results in a trans compound of the invention.

A compound of formula VI can be converted to the compound of formula

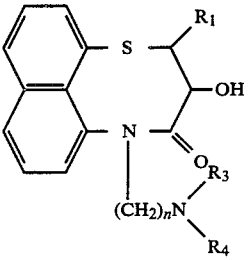

Ia wherein $R_1$, $R_3$, $R_4$ and n are as described above, by reaction with a compound of the formula

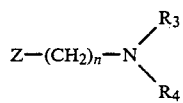

VII wherein $R_3$, $R_4$ and n are as described above, and Z is halogen, preferably chorine.

The reaction is carried out by reacting an alkali metal salt of a compound of formula VI, such as the sodium or more preferably potassium salt with an aminoalkyl halide of formula VII in a polar organic solvent such as, methyl acetate, or more preferably ethyl acetate at about 40° to about 80°, or at the reflux temperature of the solvent employed, which in the case of ethyl acetate is 77°, for a period of about 1 hour to about 17 hours. The reaction is carried out in the presence of a base such as, potassium hydroxide in acetone or more preferably potassium carbonate in acetone or in lower alkyl acetates. Separation of the compound of formula Ia can be by conventional means such as, crystallization.

A compound of the formula

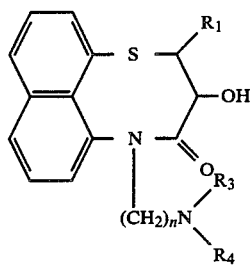

Ia wherein $R_1$, $R_3$, $R_4$ and n are as described above, which is encompassed by compounds of formula I, can be acylated by a reaction with a lower alkanoic anhydride, such as propionic anhydride, acetic anhydride, or a lower alkanoyl halide, for example, acetyl, propionyl or butyryl bromide optionally in the presence of a base such as pyridine, triethylamine, or dimethylaniline at room temperature or up to about 115°.

A resulting compound of formula I wherein $R_2$ is lower alkanoyl can be converted into the corresponding acid addition salt by treatment with an organic acid such as acetic acid, ascorbic acid, oxalic acid, malonic acid, tartaric acid, maleic acid, citric acid, lactic acid, malic acid, or fumaric acid in a suitable organic solvent, such as ethyl acetate, acetone, methanol, or ethanol. Alternatively, a compound of formula I wherein $R_2$ is lower alkanoyl can be converted into the corresponding acid addition salt by treatment with an inorganic acid such as sulfuric acid, hydrobromic acid, or more preferably hydrochloric acid, except in those instances where the $R_2$ substituent would be cleaved by such treatment.

A compound of formula I wherein $R_2$ is hydroxy, that is a compound of formula Ia, can be converted into the corresponding acid addition salt by treatment with an organic acid as described above or an inorganic acid such as hydrochloric acid in a suitable organic solvent such as ethyl acetate.

Alternatively, prior to the above described acylation and salt-forming steps, a compound of formula Ia which is produced as a racemate can be resolved into its optically active enantiomers. The resolution of a particular compound of formula Ia, that is, (±)-cis-2,3-dihydro-5-[2-(dimethylamino)ethyl]-3-hydroxy-2-(4-methoxyphenyl)naphtho[1,8-bc]-1,5-thiazocin-4(5H)-one, is shown in Formula Scheme II. The resolution of other compounds of formula Ia may require, for example, other conventional resolving agents.

FORMULA SCHEME II

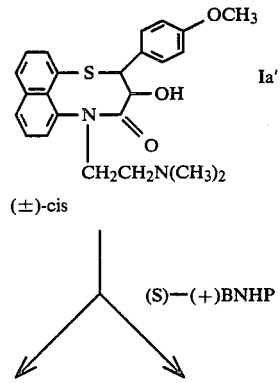

-continued (−)B.(S)—(+)BNHP
IX′

↓

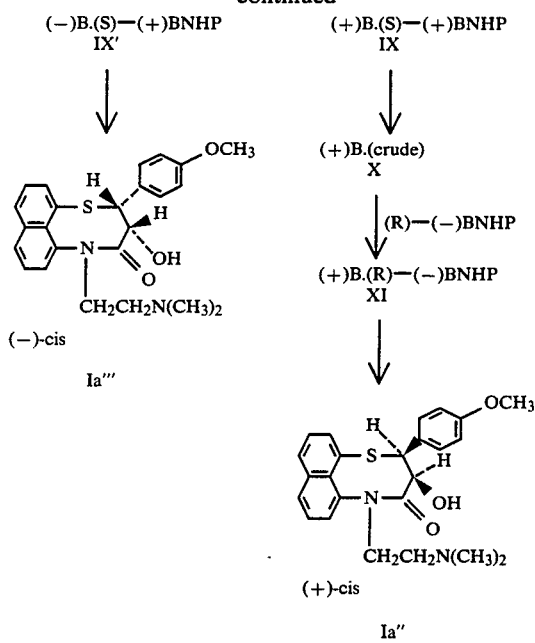

(−)-cis
Ia‴

(+)B.(S)—(+)BNHP
IX

↓

(+)B.(crude)
X

↓ (R)—(−)BNHP (+)B.(R)—(−)BNHP
XI

↓

(+)-cis
Ia″ wherein (S)-(+)BNHP is S-(+)-1,1′-binaphthyl-2,2′-diyl hydrogen phosphate; (R)-(−)BNHP is R-(−)-1,1′-binaphthyl-2,2′-diyl hydrogen phosphate; and (+)B and (−)B are respectively the (+)- and (−)-enantiomers of the racemate of formula Ia′. (±)-cis-3-(acetyloxy)-2,3-dihydro-5-[2-(dimethylamino)ethyl]-2-(4-methoxyphenyl)naphtho[1,8-bc]-1,5-thiazocin-4(5H)-one.

In connection, with Formula Scheme II above, the racemate (±)-cis-2,3-dihydro-5-[2-(dimethylamino)ethyl]-3-hydroxy-2-(4-methoxyphenyl)naphtho[1,8-bc]-1,5-thiazocin-4(5H)-one of the formula Ia′ in a lower alkanol such as, methanol, is treated with a hot methanolic solution of a resolving agent such as S-(+)-1,1′-binaphthyl-2,2′-diyl hydrogen phosphate and the resulting solution is allowed to cyrstallize at about room temperature. The crystals are a salt of formula IX′ of the resolving agent and the (−)-cis enantiomer of the compound of formula Ia′. The soluble salt is that of the (+)-cis enantiomer of the compound of formula Ia′ and the resolving agent. This is the solution of formula IX in Formula Scheme II above.

The above solution of the compound of formula IX is concentrated and treated in water with a base such as, concentrated ammonium hydroxide or sodium hydroxide and extracted with an organic solvent then concentrated to give the crude (+)-cis enantiomer of formula X of the Formula Scheme II.

The crude (+)-cis-enantiomer of formula X can be further purified by dissolving in a warm or hot solution of a lower alkanol such as methanol, and treating the resulting solution with a resolving agent such as, R(−)-1,1′-binaphthyl-2,2′-diyl hydrogen phosphate in methanol. A salt of this resolving agent and the (+)-cis enantiomer of Formula XI results.

The just above mentioned salt can be suspended in water and treated with a base such as, concentrated ammonium hydroxide, and the resulting suspension can be extracted with a polar organic solvent such as, for example, ether, methylene chloride, or ethyl acetate.

The resulting (+)-cis enantiomer of formula Ia″ can be isolated from the solution by conventional methods such as, evaporation of the solvent and crystallization of the residue.

The salt of formula IX′ can be treated with a base, such as sodium hydroxide, or more preferably ammonium hydroxide in water to generate the (−)-cis enantiomer of formula Ia‴. The (−)-cis enantiomer can be isolated from the solution by conventional methods such as extraction followed by crystallization.

Compounds of formula Ia are encompassed by formula I and thus are within the scope of the invention, and can be further treated with inorganic acids to form acid addition salts thereof as described above. Acid addition salts of compounds of formula Ia are also within the scope of the invention.

The compound of formula II, that is, 8-amino-1-naphthalenethiol can be prepared as follows. A solution of 1,8-naphthosultam, which is a known compound in diethoxyethane or more preferably dimethoxyethane is added dropwise to a solution of a reducing agent such as, sodium bis(2-methoxyethoxy)aluminum hydride or lithium aluminum hydride in toluene or anhydrous ether respectively, and stirred at reflux. The resulting mixture is acidified with an inorganic acid such as, sulfuric acid and the resulting 8-amino-1-naphthylenethiol is recovered by conventional means such as extraction followed by crystallization.

Compounds of formula III are known compounds or can be prepared according to known methods. Exemplary of compounds of formula III, which are utilized as reactants in the process of the invention are:

trans-3-(p-methoxyphenyl)glycidate; and
trans-3-(p-ethoxyphenyl)glycidate.

The compounds of formula VII are known compounds or can be prepared according to known methods. Exemplary of the compounds of formula VII are:

2-dimethylaminoethyl chloride;
2-dimethylaminoethyl bromide;
2-diethylaminoethyl chloride;
2-dipropylaminoethyl chloride; and
3-dimethylaminopropyl chloride.

The compounds of formula I including the pharmaceutically acceptable acid addition salts thereof, are calcium channel blockers, and are therefore useful as agents in lowering blood pressure and in myocardial preservation during ischemia. Their pharmacologically useful activities are demonstrated in warm-blooded animals using standard procedures which are set out below.

GUINEA PIG ILEUM ASSAY

Male guinea-pigs weighing from 300–400 grams were stunned and bled. The abdomen was opened and 10–15 cm of terminal ileum was carefully removed and cleaned and placed in Tyrode's Solution of the following composition: NaCl (8 g/l), KCl (0.2 g/l), MgCl$_2$ (0.1 g/l.), CaCl$_2$ (0.2 g/l). NaH$_2$PO$_4$ (0.05 g/l), NaHCO$_3$ (1.0 g/l) and Glucose (1 g/l). The solution was maintained at 37° C. and gassed with 95%O$_2$ and 5%CO$_2$. Portions of the ileum were placed over a glass rod, a shallow incision was made the length of the mesenteric attachment just severing the outer-longitudinal muscle layer. The longitudinal muscle was separated from the underlying circular muscle by gentle dissection (Rang, H. P. Annals of New York Academy of Science, vol. 144, page 756, 1964). The tissue was fixed at one end to a tissue holder, the other end was connected by a thread to a force transducer and suspended in a muscle bath containing Tyrode's Solution maintained at 37° C. and gassed with 95%O₂ and 5%CO₂. An initial tension of 500 mg was applied and the tissue allowed to equilibrate for 60 minutes prior to the start of the study. During this period the tissue was washed every 16 minutes. Each preparation, at 16 minute intervals, was challenged with KCl sufficient to yield a bath K⁺ concentration of 80 mMK for 2 minutes, then washed with fresh solution. The 16 minute interval between K⁺ challenges was maintained throughout the study. Upon stabilization of the responses to the K⁺ challenge the test compound (potential calcium entry antagonist) was introduced into the bath 2 minutes prior to and during the 2 minute exposure to K⁺ after which the bath was cleared and washed with fresh solution. Logarithmically increasing doses (up to $10^{-4}$M) of the potential antagonist were administered as the study progressed.

The measure of a compound's ability to inhibit the tonic contraction of muscle is a measure of its activity as a calcium channel blocking agent.

The IC$_{50}$ is that concentration at which a compound inhibits the tonic contraction of muscle by 50%.

The activity of compounds of the invention in this test is given in the table which follows.

BLOOD PRESSURE LOWERING IN THE SPONTANEOUSLY HYPERTENSIVE (SH) RAT

Six male SH rats were used for each test. Body weights were recorded. Six pre-drug control recordings of the systolic blood pressure (mmHg) were measured from the tails of the rats which were unanesthetized and restrained in holders. The rats were previously heated for 5-10 minutes at 32°-34° C. The systolic blood pressure was measured by an occlusion cuff.

The compounds were administered orally to the rats in a composition that included 5% compound and the remainder gum acacia. The blood pressure of the rats was measured over a period of hours following oral administration.

The measure of a compound's ability to decrease blood pressure, is a measure of its activity as an antihypertensive agent.

The activity of a compound of the invention in this test is given in the table which follows.

TABLE

| R₂ | Salt | | Guinea Pig Ileum Tonic IC$_{50}$ (M) | Systolic Blood Pressure in SH Rat Peak Decrease (Δ mm Hg) |
|---|---|---|---|---|
| OH | HCl | (±)-cis | 4.2 × 10⁻⁶ | |
| OCOCH₃ | HCl | (±)-cis | 3.9 × 10⁻⁶ | |
| OCOCH₃ | HCl | (±)-trans | 3.0 × 10⁻⁶ | |
| OH | HCl | (+)-cis | 3.1 × 10⁻⁶ | |
| OCOCH₃ | fumarate | (+)-cis | 2.5 × 10⁻⁷ | −66 ± 12 |

TABLE-continued

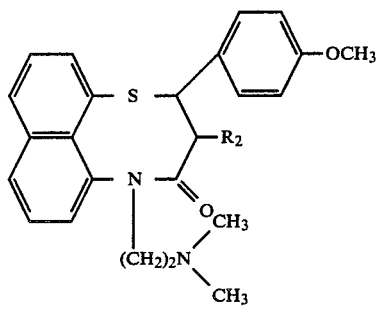

| R₂ | Salt | | Guinea Pig Ileum Tonic IC$_{50}$ (M) | Systolic Blood Pressure in SH Rat Peak Decrease (Δ mm Hg) |
|---|---|---|---|---|
| | | | | (1–6)ᵃ |

ᵃDuration of Effect on blood pressure in hours.

The compounds of formula I, and acid addition salts thereof as herein described, can be incorporated into standard pharmaceutical dosage forms. The compounds of formula I, are useful for oral or parenteral application with the usual pharmaceutical carrier materials, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, or capsules, or in liquid form, for example as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The invention also relates to a method of lowering blood pressure or of bringing about myocardial preservation during ischemia, which comprises administering an effective amount of a compound of formula I, or pharmaceutically acceptable acid addition salts thereof to a warm-blooded animal in need of such treatment. The amount of an oral daily dosage for compounds of formula I can be determined by one skilled in the art and would be comparable to that of diltiazem. The amount of an intravenous dosage can also be determined by one skilled in the art and is comparable to that of diltiazem. It is to be understood, however, that dosages may vary from individual to individual and accordingly the above recitation is not intended to limit the scope of the present invention in any way.

The following examples further illustrate the invention. All temperatures are in degrees C., unless otherwise mentioned.

EXAMPLE 1

8-Amino-1-naphthalenethiol

To a solution of 2.0 g of 1,8-naphthosultam in 7 mL of dimethoxyethane was added dropwise under gentle reflux a solution of 11.5 mL of sodium bis(2-methoxyethoxy)aluminum hydride in toluene (3.4 mol solution in toluene) over a period of 15 minutes, then stirred at reflux for 17 hours. The mixture was cooled in an icebath, 5 mL of water were added dropwise then the solution was neutralized with 4N sulfuric acid (pH ~7) and extracted with ether (3×75 mL). The combined ether solutions were washed with water (75 mL) then dried (magnesium sulfate) and removal of the solvent gave 1.5 g of 8 -amino-1-napthalenethiol. The thiol was recrystallized from ether—petroleum ether to afford 1.3 g of 8-amino-1-naphthalenethiol, mp. 69°–72°.

Calculated: C, 68.56; H, 5.18; N, 8.00. Found: C, 68.42; H, 5.05; N, 7.84.

EXAMPLE 2

8-Amino-1-naphthalenethiol

To a mixture of 3.0 g of lithium aluminum hydride in 150 mL of anhydrous ether was added dropwise a solution of 4.0 g of 1,8-naphthosultam in 15 mL of anhydrous tetrahydrofuran over a period of 45 minutes while maintaining a gentle reflux. After completion of the addition, the yellow mixture was refluxed for another hour. The mixture was cooled in an ice-bath and the excess of lithium aluminum hydride was destroyed by dropwise addition of 10 mL of water. The resulting mixture was acidified with 200 mL of 4N sulfuric acid and extracted with ether (3×100 mL). The ether extracts were washed with water (75 mL) and dried (magnesium sulfate). Removal of the solvent gave 2.7 g (79%) of 8-amino-1-naphthalenethiol, mp. 68°–70°. This compound is sensitive to air, and therefore was used immediately.

EXAMPLE 3

(±)-erythro- and threo-3-[(8-Amino-1-naphthalenyl)-thio]-2-hydroxy-3-(4-methoxyphenyl)propanoic Acid Methyl Esters A mixture of 5.0 g of 8 amino-1-naphthalenethiol and 7.1 g of trans-3-(p-methoxyphenyl)glycidate was stirred and heated at 110° (oil bath) under nitrogen for 40 minutes. The solvent was removed under reduced pressure to give 13.0 g of a residue, of which was purified by column chromatography on silica gel (122 g). The column was eluted with 100 mL portions of methylene chloride, and methylene chloride—ether (95:5), to give 7.4 g (68%) of a mixture of the title isomeric esters [Nuclear magnetic resonance analysis indicated a 1:3 ratio of erythro:threo-esters]. This mixture was used without further purification for the preparation of the corresponding erythro- and threo-acids, (±)-erythro-3-[(8-amino-1-naphthalenyl)thio]-2-hydroxy-3-(4-methoxyphenyl)propanoic acid, and (±)-threo-3-[(8-amino-1-naphthalenyl)thio]-hydroxy3-(4-methoxyphenyl)-propanoic acid respectively.

EXAMPLE 4

(±)-erythro- and threo-3-[(8-Amino-1-naphthalenyl)-thio]-2-hydroxy-3-(4-methoxyphenyl)propanoic Acid Methyl Esters Under nitrogen, a mixture of 5.8 g of 2-amino1-naphthalenethiol and 6.1 g of trans-3-(p-methoxyphenyl)-glycidate in 60 mL toluene was stirred and heated at reflux over a period of 17 hours. The solvent was removed under reduced pressure to give 12.3 g of a residue, which was purified by column chromatography as described in the previous example to give 2.7 g (21%) of a mixture of the title isomeric esters [Nuclear magnetic resonance analysis indicated a 2:1 ratio of erythro:threo-esters]. This mixture was used without further purification for the preparation of the corresponding erythro- and threo-acids of Example 3 above.

EXAMPLE 5

Isolation of (±)-erythro-3-[(8-Amino-1-naphthalenyl)-thio]-2-hydroxy-3-(4-methoxyphenyl)propanoic Acid Methyl Ester A mixture of 12.0 g of (±)-erythro- and threo-3-[(8-amino-1-naphthalenyl)thio]-2-hydroxy-3-(4-methoxyphenyl)propanoic acid methyl esters, prepared under identical reaction conditions as in Example 4, was chromatographed on a column using 122 g of silica gel and eluted with methylene chloride—ether gradient to give 4.1 g of (±)-erythro-3-[(8-amino-1-naphthalenyl)thio]2-hydroxy-3-(4-methoxyphenyl)propanoic acid methyl ester. A sample of this compound was recrystallized from ether, mp. 110°–112°.

Calculated: C, 65.78; H, 5.52; N, 3.65. Found: C, 65.40; H, 5.47; N, 3.56.

EXAMPLE 6

Isolation of (±)-erythro- and threo-3-[(8-Amino-1-naphthalenyl)thio]-2-hydroxy-3-(4-methoxyphenyl)-propanoic Acids A mixture of 2.5 g of a mixture of (±)-erythro- and threo-esters and 30 mL 1N sodium hydroxide in 10 mL of ethanol was heated at reflux for 20 minutes. After cooling it was acidified with 6N hydrochloric acid and the precipitate was filtered, washed with water, then dried to give 2.4 g of the acids of the title. The mixture was dissolved in methanol at room temperature and treated with charcoal, filtered and the solvent was removed under reduced pressure. The residue was crystallized first from methylene chloride, then acetonitrile to afford 0.50 g (21%) of pure (±)-erythro-3-[(8-amino-1-naphthalenyl)thio]-2-hydroxy-3-(4-methoxyphenyl)-propanoic acid, mp. 181°–182°.

Calculated: C, 65.03; H, 5.19; N, 3.79. Found: C, 64.75; H, 5.23; N, 3.68.

The combined mother liquors obtained in the separation of the erythro compound described above were concentrated to dryness to give 1.9 g of the crude title threo-acid. The crude acid was dissolved in ethyl acetate and the solution was extracted with 1N HCl (3×40 mL). The combined aqueous solutions were extracted with ether (20 mL) then adjusted to pH 5 with 10% sodium hydroxide and the crude (±)-threo-3-[(8-amino-1-naphthalenyl)thio]-2-hydroxy-3-(4-methoxyphenyl)-propanoic acid was isolated by filtration, yield: 1.0 g (40%), mp 115°–117° as the hydrate.

Calculated: C, 62.00; H, 5.47; N, 3.61. Found: C, 62.16; H, 5.47; N, 3.44.

EXAMPLE 7

Base Catalyzed Reaction of 8-Amine-1-naphthalene-thiol with trans-3-(p-methoxyphenyl)glycidate Under nitrogen a mixture of 2.6 g of 8-amine-1-naphthalenethiol 3.0 g of trans-3-(p-methoxyphenyl)glycidate and 0.3 g of potassium carbonate in 40 mL acetonitrile was stirred at reflux over a period of 3 hours. The solvent was removed under reduced pressure and the residue (5.6 g) was chromatographed on a column using 85 g of silica gel. The column was eluted with 40 mL portions of methylene chloride. The first seven fractions were collected and the solvent was removed under reduced pressure gave 2.0 g (37%) of crude 2,3-dihydro-2-(4-methoxyphenyl)naphthol[1,8-de]1,3-thiazocine-2-acetic acid methyl ester which was recrystallized from ether—pet. ethers to afford 0.9 g (17%) of pure ester, mp 99°–100°.

(±)-threo-3-[(8-Amino-1-naphthalenyl)thio]-2-hydroxy-3-(4-methoxy-phenyl)propanoic acid methyl ester was obtained from the silica gel column by changing the solvent to methylene chloride—ether (75:25). The methylene chloride—ether fractions 19–25 of which were collected, and solvents were removed under reduced pressure to give 1.7 g (30%) of crude (±)-threo-3-[(8-amino-1-naphthalenyl)thio]-2-hydroxy-3-(4-methoxyphenyl)propanoic acid methyl ester. For analysis, a sample of this compound was crystallized from ether-pet. ether, mp 118°–119°.

Calculated: C, 65.78; H, 5.52; N, 3.65. Found: C, 65.59; H, 5.62; N, 3.41.

EXAMPLE 8

(±)-threo-3-[(8-Amino-1-naphthalenyl)thio]-2-hydroxy-3-(4-methoxyphenyl)propanoic Acid A mixture of 5.0 g of (±)-threo-3-[(8-amino-1-naphthalenyl)thio]-2-hydroxy-3-(4-methoxyphenyl)-propanoic acid methyl ester and 60 mL 1N sodium hydroxide in 20 mL of ethanol was heated at reflux for 20 minutes. Most of the ethanol was removed under reduced pressure, then diluted with water (75 mL) and extracted with ether (2×40 mL). The aqueous solution was treated with charcoal, filtered and the filtrate acidified with 6N HCl. The crystals were separated by filtration (9.0 g) then made a slurry in 150 mL methanol and filtered off to give 1.5 g (31%) of (±)-threo3-[(8-amino-1-naphthalenyl)-thio]-2-hydroxy-3-(4-methoxyphenyl)-propanoic acid, mp 115°–117°.

EXAMPLE 9

(±)-trans-2,3-Dihydro-5-[2-(dimethylamino)ethyl]-3-hydroxy-2-(4-methoxyphenyl)naphtho[1,8-bc]-1,5-thiazocin-4(5H)-one A mixture of 0.415 g of sodium hydride (58% dispersion in mineral oil) in 50 mL dimethyl sulfoxide (dried over CaH$_2$) was stirred under nitrogen at 70° (bath temperature) for 1 hour then allowed to cool to room temperature. To this mixture 2.8 g of (±)-trans-2,3-dihydro-3-hydroxy-2-(4-methoxyphenyl)naphtho[1,8-bc]-1,5-thiazocin-4(5H)-one was added then stirred at room temperature for 30 minutes. After the dropwise addition of 1.2 g of 2-dimethylaminoethyl chloride in 10 mL dimethyl sulfoxide, the mixture was heated at 50° for 30 minutes, then poured on 50 mL of ice-water. The aqueous solution was extracted with ethyl acetate (3×40 mL). The combined extracts were washed with brine (40 mL) and dried (magnesium sulfate). Removal of the solvent gave 3.1 g (92%) of crude (±)-trans-2,3-dihydro-5[2-(dimethylamino)ethyl]-3-hydroxy-2-(4-methoxyphenyl)naphtho[1,8-bc]-1,5-thiazocin-4(5H)-one. For analysis a sample of this compound was crystallized from ethyl acetate, mp 157°–158°.

Calculated: C,68.23; H, 6.20; N, 6.63. Found: C,67.96; H, 6.42; N, 6.43.

The above base (3.1 g), on treatment with hydrogen chloride (anhydrous) in ethyl acetate afforded the crude hydrochloride which was separated by filtration, washed with acetone and dried to give 2.4 g (71%) of (±)-trans-2,3-dihydro-5-[2-dimethylamino)ethyl]-3-hydroxy-2-(4-methoxyphenyl)naphtho[1,8-bc]-1,5-thiazocin-4(5H)-one hydrochloride as the semihydrate, mp 95°–97° (water free sample mp 239°–241°).

Calculated: C, 61.58; H, 6.03; N, 5.98. Found: C, 61.21; H, 6.13; N, 5.83.

EXAMPLE 10

(±)-trans-3-(Acetyloxy)-2,3-dihydro-5-[2-(dimethylamino)ethyl]-2-(4-methoxyphenyl)naphtho[1,8-bc]-1,5-thiazocin-4(5H)-one A mixture of 6.3 g of (±)-trans-2,3-dihydro-5-[2-(dimethylamino)ethyl]-2-(4-methoxyphenyl)naphtho[1,8-bc]-1,5-thiazocin-4(5H)-one hydrochloride and 130 mL of acetic anhydride was heated at 100° for 17 hours. The excess of reagent was removed under reduced pressure then to the residue ice-water (50 mL) was added and made basic with concentrated ammonium hydroxide. The aqueous suspension was extracted with ethyl acetate (3×70 mL) and the combined extracts were dried (magnesium sulfate). Removal of the solvent gave 6.3 g (98%) of (±)-trans-3-(acetyloxy)-2,3-dihydro-5-[2-(dimethylamino)ethyl]-2-(4-methyoxyphenyl)naphtho[1,8-bc]-1,5-thiazocin-4(5H)-one. For analysis a sample of this compound was crystallized from ether, mp 156°–157°.

Calculated: C, 67.22; H, 6.08; N, 6.03. Found: C, 66.76; H, 6.63; N, 5.64.

The above base (6.5 g) on treatment with hydrogen chloride (anhydrous) in acetone, afforded 6.5 g (92%) of (±)-trans-3-(acetyloxy)-2,3-dihydro-5-[2-(dimethylamino)ethyl]-2-(4-methoxy-phenyl)-naphtho[1,8-bc]-1,5-thiazocin4(5H)-one hydrochloride, mp 264°–266°. For analysis a sample was recrystallized from acetone, mp 266°–267°.

Calculated: C, 62.33; H, 5.83; N, 5.59. Found: C, 62.36; H, 5.83; N, 5.63.

EXAMPLE 11

Isolation of the (±)-erythro-3-[(8-Amino-1-naphthalenyl)thio]-2-hydroxy-3-(4-methoxyphenyl)-propanoic Acid A mixture of 1.9 g of (±)-erythro- and threo-3-[(8-amino-1-naphthalenyl)thio]-2-hydroxy-3-(4-methoxyphenyl)-propanoic acid methyl esters prepared as in Example 4, and 30 mL 1N sodium hydroxide in 10 mL ethanol was heated at reflux for 20 minutes. After cooling it was diluted with water (60 mL) and extracted with ether (2×30mL). The aqueous solution was treated with charcoal, filtered and the filtrate was neutralized with 6N hydrochloric acid. The crystals were collected by filtration and recrystallized first from methylene chloride, then from acetonitrile to give 0.5 g (28%) of (±)-erythro-3-[(8-amino-1-naphthalenyl)thio]-2-hydroxy-3-(4-methoxyphenyl)propanoic acid, mp. 181°–182°.

EXAMPLE 12

(±)-Erythro-3-[(8-Amino-1-naphthalenyl)thio]-2-hydroxy-3-(4-methoxyphenyl)propanoic Acid Methyl Ester To a solution of 0.5 g of (±)-erythro-3-[(8-amino-1-naphthalenyl)thio]-2-hydroxy-3-(4-methoxyphenyl)-propanoic acid in 50 mL methanol, 3 drops of concentrated sulfuric acid was added and heated at reflux for one hour. The reaction mixture was cooled to room temperature, diluted with water (100 mL) and extracted with ether (3×200 mL). The combined ether extracts were washed with water (200 mL), dried (magnesium sulfate) and removal of the solvent gave the product which was crystallized from ether to afford 0.5 g (98%) of (±)-erythro-3-[(8-amino-1-naphthalenyl)thio]-2-hydroxy-3-(4-methoxyphenyl)propanoic acid methyl ester, mp. 110°–112°.

EXAMPLE 13

Cyclization of (±)-threo-3-[(8-Amino-1-naphthalenyl)-thio]-2-hydroxy-3-(4-methoxyphenyl)propanoic Acid A mixture of (±)-threo-3-[8-amino-1-naphthalenyl)-thio]-2-hydroxy-3-(4-methoxyphenyl)propanoic acid 0.8 g in 25 mL xylene was heated at reflux for 3 hours while the water was removed by continuous azeotropic distillation. The solvent was evaporated at reduced pressure and the residue was crystallized from ethyl acetate to give 0.7 g (92%) of (±)-trans-2,3-dihydro-3-hydroxy-2-(4-methoxy-phenyl)naphtho[1,8-bc]-1,5-thiazocin-4-one, mp 247°–248°.

Calculated: C, 68.37; H, 4.83; N, 3.99. Found: C, 68.00; H, 4.83; N, 4.04.

EXAMPLE 14

(±)-cis-2,3-Dihydro-3-hydroxy-2-(4-methoxyphenyl)-naphtho[1,8-bc]-1,5-thiazocin-4(5H)-one To a solution of 0.9 g of (±)-erythro-3-[(8-amino-1-naphthalenyl)thio]-2-hydroxy-3-(4-methoxyphenyl)-propanoic acid and 0.4 mL of triethylamine in 45 mL of dimethylformamide was added dropwise a solution of 1.05 g of 2-iodo-1-methylpyridinium iodide in 25 mL of dimethylformamide over a period of 30 minutes. The reaction mixture was stirred at room temperature for 17 hours and concentrated to dryness at 50° in vacuo. To the residue, water and 1N hydrochloric acid were added and the aqueous solution was extracted with chloroform. The chloroform solution was dried (magnesium sulfate) and removal of the solvent gave the product which was crystallized from chloroform to afford 0.650 g (76%) of (±)-cis-2,3-dihydro-3-hydroxy-2-(4-methoxyphenyl)naphtho[1,8-bc]-1,5-thiazocin4-(5H)-one, mp 214°–215°. A sample was recrystallized from ethyl acetate, mp 218°–219°.

Calculated: C, 68.36; H, 4.88; N, 3.99. Found: C, 68.19; H, 5.01; N, 4.04.

EXAMPLE 15

(±)-cis-2,3-Dihydro-5-[2-(dimethylamino)ethyl]-3-hydroxy-2-(4-methoxyphenyl)naphtho[1,8-bc]-1,5-thiazocin-4(5H)-one A mixture of 1.1 g of (±)-cis-2,3-dihydro-3-hydroxy2-(4-methoxyphenyl)naphtho[1,8-bc]-1,5-thiazocin-4(5H)-one, 0.48 g of powdered potassium carbonate and 0.425 g of 2-dimethylaminoethyl chloride in 25 mL of ethyl acetate was stirred and heated at reflux for 3 hours, then twice an additional 0.10 g of 2-dimethylaminoethyl chloride was added at 3 hour intervals. The mixture was heated at reflux for a total of 17 hours then was cooled to room temperature and filtered. The filtrate was diluted with 40 mL of ethyl acetate and washed with brine (40 mL) and dried (magnesium sulfate). Removal of the solvent gave 1.2 g (92%) of (±)-cis-2,3-dihydro-5-[2-(dimethylamino)ethyl]-3-hydroxy-2-(4-methoxyphenyl)naphtho[1,8-bc]-1,5-thiazocin-4(5H)- one. A sample of this compound was crystallized from ethyl acetate, mp. 121°–122°.

Calculated: C, 68.22; H, 6.20; N, 6.63. Found: C, 68.00; H, 6.14; N, 6.55.

The above base (1.2g) on treatment with hydrogen chloride (anhydrous) in ethyl acetate afforded the hydrochloride which after recrystallization from ethanol gave 1.1 g (85%) of (±)-cis-2,3-dihydro-5-[2-(dimethylamino)ethyl]-3-hydroxy-2-(4-methoxyphenyl)naphtho[1,8-bc]-1,5-thiazocin-4(5H)-one hydrochloride, mp 167°–168°.

Calculated: C, 62.80; H, 5.93; N, 6.10. Found: C, 62.53; H, 6.03; N, 6.17.

EXAMPLE 16

(±)-cis-3-(Acetyloxy)-2,3-dihydro-5-[2-dimethylamino)ethyl]-2-(4-methoxyphenyl)naphtho[1,8-bc]-1,5-thiazocin-4(5H)-one A mixture of 0.4 g of (±)-cis-2,3-dihydro-5-[2-(dimethylamino)ethyl]-3-hydroxy-2-(4-methoxyphenyl)naphtho[1,8-bc]-1,5-thiazocin-4-(5H)-one hydrochloride and 8 mL of acetic anhydride was heated at 100° for 17 hours. The reaction mixture was concentrated to dryness and to the residue water, followed by concentrated ammonium hydroxide were added. The aqueous suspension was extracted with ethyl acetate. The ethyl acetate solution was washed with brine, dried (magnesium sulfate) and removal of the solvent gave 0.4 g (99%) of (±)-cis-3-(acetyloxy)-2,3-dihydro-5-[2-(dimethylamino)ethyl]-2-(4-methoxyphenyl)naphtho[1,8-bc]-1,5-thiazocin-4(5H)-one. A sample of this compound was crystallized from ether, mp. 111°–112°.

Calculated: C, 67.22; H, 6.08; N, 6.03. Found: C, 67.31; H, 6.08; N, 5.91.

The above base (0.2 g) on treatment with hydrogen chloride (anhydrous) in ethyl acetate afforded the hydrochloride, which was recrystallized from acetone—ethyl acetate to give 0.21 g of (±)-cis-3-(acetyloxy)-2,3-dihydro-5-[2-dimethylamino)ethyl]-2-(4-methoxyphenyl)naphtho[1,8-bc]-1,5-thiazocin-4(5H)-one hydrochloride, mp. 193°–194°.

Calculated: C, 62.33; H, 5.83; N, 5.59. Found: C, 61.99; H, 5.99; N, 5.56.

EXAMPLE 17

Resolution of (±)-cis-2,3-Dihydro-5-[2-(dimethylamino)ethyl]-3-hydroxy-2-(4-methoxyphenyl)-naphtho[1,8-bc]-1,5-thiazocin-4(5H)-one A hot solution of 10.3 g of (±)-cis-2,3-dihydro-5-[2-(dimethylamino)ethyl]-3-hydroxy-2-(4-methoxyphenyl)naphtho [1,8-bc]-1,5-thiazocin-4(5H)-one in 25 mL of methanol was combined with a hot solution of 8.49 g of S-(+)-1,1′-binaphthyl-2,2′-diyl hydrogen phosphate in 300 mL of methanol. The clear solution was allowed to crystallize at room temperature for 17 hours. The crystals were then collected by filtration, washed with methanol and dried, thus affording 7.7 g (82%) of (−)-cis-2,3-dihydro-5-[2-(dimethylamino)ethyl]-3-hydroxy-2-(4-methoxyphenyl)naphtho[1,8-bc]-1,5-thiazocin-4(5H)-one S-(+)-1,1′-binaphthyl-2,2′-diyl hydrogen phosphate, mp. 286°–288°. (d), $[\alpha]_D^{25} + 174.4°$ (C 0.45, methanol).

EXAMPLE 18

(−)-cis-2,3-Dihydro-5-[2-(dimethylamino)ethyl]-3-hydroxy-2-(4-methoxyphenyl)naphtho[1,8-bc]-1,5-thiazocin-4(5H)-one (−)-cis 2,3-Dihydro-5-[2-(dimethylamino)ethyl]-3-hydroxy-2-(4-methoxyphenyl)naphtho[1,8-bc]-1,5-thiazocin-4(5H)-one S-(+)-1,1'-binaphthyl-2,2'-diyl hydrogen phosphate, 7.6 g in 70 mL of water was decomposed with concentrated ammonium hydroxide. The resulting suspension was extracted with ether (2×250 mL). The combined ether solutions were washed with water (50 mL) and dried (magnesium sulfate). Removal of the solvent gave 4.05 g (97%) of (−)-cis-2,3-dihydro-5-[2-(dimethylamino)ethyl]-3-hydroxy-2-(4-methoxyphenyl)naphtho[1,8-bc]-1,5-thiazocin-4(5H)-one. A sample was crystallized from ether—petroleum ether, mp. 98°-100°, $[\alpha]_D^{25}$ −227.55° (C 0.31, methanol) A 100 MHz NMR spectrum of the title compound in CDCl$_3$, in the presence of chiral shift reagent Fu(TFC)$_3$ indicated that the sample is enantiomerically pure.

A sample of the above base, on treatment with hydrogen chloride (anhydrous) in ethyl acetate gave the hydrochloride, which after recrystallization from ethanol-ether afforded pure (−)-cis-2,3-dihydro-5-[2-(dimethylamino)ethyl]-3-hydroxy-2-(4-methoxyphenyl)naphtho[1,8-bc]-1,5-thiazocin-4(5H)-one hydrochloride, mp. 204°-206°, $[\alpha]_D^{25}$ −181.17° (C 0.43, MeOH).

Calculated: C, 62.80; H, 5.93; N, 6.10. Found: C, 62.73; H, 6.15; N, 6.01.

EXAMPLE 19

(+)-cis-2,3-Dihydro-5-[2-(dimethylamino)ethyl]-3-hydroxy-2-(4-methoxyphenyl)naphtho[1,8-bc]-1,5-thiazocin-4(5H)-one R-(−)-1,1'-binaphthyl-2,2'-diyl Hydrogen Phosphate The combined mother liquors obtained in the preparation of (−)-base S-(+)-1,1'-binaphthyl-2,2'-diyl hydrogen phosphate were concentrated to dryness. The residue in 70 mL of water was decomposed with concentrated ammonium hydroxide, and the resulting suspension was extracted with ether (2×250 mL). The combined extracts were washed with water (50 mL) and dried (magnesium sulfate). Removal of the solvent gave 5.6 g of crude (+)-cis-2,3-dihydro-5-[2-(dimethylamino)ethyl]-3-hydroxy-2-(4-methoxyphenyl)naphtho[1,8-bc]-1,5-thiazocin-4(5H)-one. The above base (5.6 g) was dissolved in 15 mL of hot methanol and combined with a hot solution of 4.6 g of R-(−)-1,1'-binaphthyl-2,2'-diyl hydrogen phosphate in 160 mL of methanol. The solution was allowed to crystallize at room temperature for 17 hours. The crystals were collected by filtration, washed with methanol and dried, thus affording 8.1 g (79%) of (+)-cis-2,3-dihydro-5-[2-(dimethylamino)ethyl]-3-hydroxy-2-(4-methoxyphenyl)naphtho[1,8-bc]-1,5-thiazocin-4(5H)-one R-(−) 1,1'-binaphthyl-2,2'-diyl hydrogen phosphate, mp. 287°-289° (d), $[\alpha]_D^{25}$ −172.4° (C 0.41, methanol)

Calculated: C, 68.56; H, 5.10; N, 3.63. Found: C, 68.30; H, 5.02; N, 3.39.

EXAMPLE 20

(+)-cis-2,3-Dihydro-5-[2-(dimethylamino)ethyl]-3-hydroxy-2-(4-methoxyphenyl)naphtho[1,8-bc]-1,5-thiazocin-4(5H)-one (+)-cis-2,3-Dihydro-5-[2-(dimethylamino)ethyl]-3-hydroxy-2-(4-methoxyphenyl)naphtho[1,8-bc]-1,5-thiazocin-4(5H)-one R-(−)-1,1'-binaphthyl-2,2'-dihyl hydrogen phosphate, 8.1 g in 80 mL of water was decomposed with concentrated ammonium hydroxide. The resulting suspension was extracted with ether (3×200 mL). The combined ether solutions were washed with water (200 mL) and dried (magnesium sulfate). Removal of the solvent gave 4.20 g (95%) of (+)-cis-2,3-dihydro-5-[2-(dimethylamino)ethyl]-3-hydroxy-2-(4-methoxyphenyl)naphtho[1,8-bc]-1,5-thiazocin-4(5H)-one. An analytical sample was crystallized from ether—petroleum ether, mp. 98°-100°, $[\alpha]_D^{25}$ +233.1° (C 0.41, methanol).

Calculated: C, 68.23; H, 6.20; N, 6.63. Found: C, 68.09; H, 6.20; N, 6.63.

A sample of the above base, on treatment with hydrogen chloride (anhydrous) in ethyl acetate, gave the hydrochloride, which after recrystallization from ethanol—ether afforded pure (+)-cis-2,3-dihydro-5-[2-(dimethylamino)ethyl]-3-hydroxy-2-(4-methoxyphenyl)naphtho[1,8-bc]-1,5-thiazocin-4(5H)-one hydrochloride, mp. 206°-208°, $[\alpha]_D^{25}$ +181.02° (C 0.48, methanol).

Calculated: C, 62.80; H, 5.93; N, 6.10. Found: C, 62.48; H, 5.84; N, 6.02.

EXAMPLE 21

(−)-cis-3-(Acetyloxy)-2,3-dihydro-5-[2-(dimethylamino)ethyl]-2-(4-methoxyphenyl)naphtho[1,8-bc]-1,5-thiazocin-4(5H)-one A mixture of 3.2 g of (−)-cis-2,3-dihydro-5-[2-(dimethylamino)ethyl]-3-hydroxy-2-(4-methoxyphenyl)naphtho[1,8-bc]-1,5-thiazocin-4(5H)-one hydrochloride and 60 mL of acetic anhydride was stirred under nitrogen at 100° for 17 hours. The excess reagent was removed under reduced pressure and to the residue ice-water was added. The resulting suspension was made basic with concentrated ammonium hydroxide and extracted with ethyl acetate (2×50 mL). The combined extracts were washed with brine (50 mL) and dried (magnesium sulfate). Removal of the solvent under reduced pressure gave 3.2 g (99%) of (−)-cis-3-(acetyloxy)-2,3-dihydro-5-[2-(dimethylamino)ethyl]-2-(4-methoxyphenyl)naphtho[1,8-bc]-1,5-thiazocin-4(5H)-one as an amorphous compound, $[\alpha]_D^{25}$ −190.81° (C 0.48, methanol).

Calculated: C, 67.22; H, 6.08; N, 6.03. Found: C, 67.16; H, 6.12; N, 5.96.

The above base, (2.6 g) on treatment with fumaric acid 0.650 g in acetone afforded the fumarate, which after recrystallization from ethanol gave 3.1 g (97%) of (−)-cis-3-(acetyloxy)-2,3-dihydro-5-[2-(dimethylamino)ethyl]-2-(4-methoxyphenyl)naphtho[1,8-bc]-1,5-thiazocin-4(5H)-one (E)-2-butenedioate, mp 220°-221°, $[\alpha]_D^{25}$ −155.13° (C 0.52, methanol).

Calculated: C, 62.06; H, 5.56; N, 4.83. Found: C, 61.91; H, 5.55; N, 4.78.

EXAMPLE 22

(+)-cis-3-(Acetyloxy)-2,3-dihydro-5-[2-(dimethylamino)ethyl]-2-(4-methoxyphenyl)naphtho[1,8-bc]-1,5-thiazocin-4(5H)-one A mixture of 3.4 g of (+)-cis-2,3-dihydro-5-[2-(dimethylamino)ethyl]-3-hydroxy-2-(4-methoxyphenyl)naphtho[1,8-bc]-1,5-thiazocin-4(5H)-one hydrochloride and 60 mL of acetic anhydride was stirred under nitrogen at 100° for 17 hours. The excess of reagent was removed under reduced pressure, then to the residue ice-water was added and made basic with 10% sodium hydroxide. The resulting suspension was extracted with ether (3×75 mL) and the combined ether solutions were washed with brine and dried (magnesium sulfate). Removal of the solvent under reduced pressure gave 3.1 g (90%) of (+)-cis-3-(acetyloxy)-2,3-dihydro-5-[2-(dimethylamino)ethyl]-2-(4-methoxyphenyl)naphtho[1,8-bc]-1,5-thiazocin-4(5H)-one as an amorphous compound, $[\alpha]_D^{25}+187.94°$ (C 0.47, methanol).

Calculated: C, 67.22; H, 6.08; N, 6.03. Found: C, 67.21; H, 6.23; N, 5.97.

The above base (3.1 g), on treatment with fumaric acid 0.8 g in acetone afforded the fumarate, which after recrystallization from ethanol gave 3.7 g (95%) of (+)-cis-3-(acetyloxy)-2,3-dihydro-5-[2-(dimethylamino)ethyl]-2-(4-methoxyphenyl)naphtho[1,8-bc]-1,5-thiazocin-4(5H)-one (E)-2-butenedioate, mp 220°–221°, $[\alpha]_D^{25}+154.68°$ (C 0.53, methanol)

Calculated: C, 62.06; H, 5.56; N, 4.83. Found: C, 61.88; H, 5.62; N, 4.98.

EXAMPLE 23

| | CAPSULES | | |
|---|---|---|---|
| | | mg/capsule | |
| Item | Ingredient | 100 mg | 200 mg |
| 1. | (+)-cis-3-(Acetyloxy)-2,3-dihydro-5-[2-(dimethylamino)ethyl]-2-(4-methoxyphenyl)naphtho[1,8-bc]-1,5-thiazocin-4(5H)—one (E)—2-butenedioate | 100 | 200 |
| 2. | Corn Starch (Pregelatinized) | 50 | 80 |
| 3. | Modified Starch | 10 | 20 |
| 4. | Talc | 20 | 20 |
| 5. | Magnesium Stearate | 1 | 2 |
| | | 181 mg | 322 mg |

1. Mix Items 1–3 and wet granulate with water. Dry at 45° C. overnight.
2. Mill through suitable screen using appropriate milling equipment.
3. Add Items 4 and 5 and mix for five minutes.
4. Fill into suitable capsule.

EXAMPLE 24

| | TABLETS | | |
|---|---|---|---|
| | | mg/tablet | |
| Item | Ingredient | 100 mg | 200 mg |
| 1. | (+)-cis-3-(Acetyloxy)-2,3-dihydro-5-[2-(dimethylamino)ethyl]-2-(4-methoxyphenyl)naphtho[1,8-bc]-1,5-thiazocin-4(5H)—one(E)—2-butenedioate | 100 | 200 |
| 2. | Lactose | 100 | 200 |
| 3. | Polyvinylpyrrolidone (PVP) | 10 | 20 |
| 4. | Modified Starch | 10 | 20 |
| 5. | Magnesium Stearate | 3 | 6 |
| | | 223 mg | 446 mg |

1. Mix Items 1, 2 and 4 and granulate with PVP in water or alcohol.
2. Dry the granulation at 45° C.
3. Mill the dried granulation through a suitable mill.
4. Add Item 5 and mix for three minutes and compress on a suitable press.

EXAMPLE 25

| PARENTERAL SOLUTION | |
|---|---|
| Ingredients | mg/ml |
| (±)-cis-3-(Acetyloxy)-2,3-dihydro-5-[2-(dimethylamino)ethyl]-2-(4-methoxyphenyl)naphtho[1,8-bc]-1,5- | 10 |

| -continued | |
|---|---|
| PARENTERAL SOLUTION | |
| Ingredients | mg/ml |
| thiazocin-4(5H)—one hydrochloride | |
| Benzyl Alcohol | 10 |
| Sorbitol | 38 |
| Hydrochloric Acid q.s. to pH | 3–7 |
| Sodium Hydroxide q.s. to pH | 3–7 |
| Water for Injection q.s. to | 1 ml |

As used above, q.s. means sufficient quantity.

We claim:

1. A compound of the formula

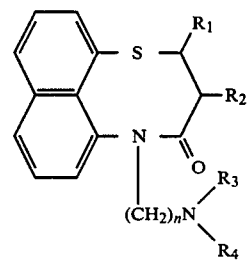

I wherein $R_1$ is phenyl substituted with 1 to 3 lower alkoxy groups or 1 to 3 halogens; $R_2$ is hydroxy or lower alkanoyloxy; $R_3$ and $R_4$ are independently lower alkyl or together form a pyrrolidine or piperidine ring, and n is 2 to 4;

or a pharmaceutically acceptable acid addition salt thereof.

2. A compound in accordance with claim 1, of the formula

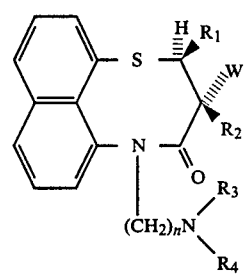

$I^I$ wherein $R_1$ is phenyl substituted with 1 to 3 lower alkoxy groups or 1 to 3 halogens; $R_2$ is hydroxy or lower alkanoyloxy; $R_3$ and $R_4$ are independently lower alkyl or together form a pyrrolidine or piperidine ring, and n is 2 to 4;

an enantiomer or a racemate thereof or a pharmaceutically acceptable acid addition salt thereof.

3. A compound in accordance with claim 2, of the formula

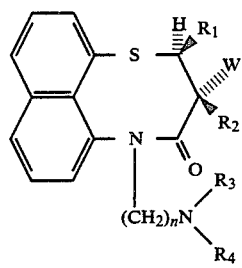

I<sup>I</sup> wherein $R_1$ is phenyl substituted with 1 to 3 lower alkoxy groups or 1 to 3 halogens; $R_2$ is hydroxy or lower alkanoyloxy; and $R_3$ and $R_4$ are independently lower alkyl or together form a pyrrolidine or piperidine ring, and n is 2 to 4 or a pharmaceutically acceptable acid addition salt thereof.

4. A compound in accordance with claim 2, wherein $R_1$ is 4-lower alkoxyphenyl and $R_2$ is hydroxy.

5. A compound in accordance with claim 4, wherein $R_1$ is 4-methoxyphenyl and $R_3$ and $R_4$ are independently lower alkyl and n is 2 to 3.

6. A compound in accordance with claim 5, (+)-cis-2,3-dihydro-5-[2-(dimethylamino)ethyl]-3-hydroxy-2-(4-methoxyphenyl)naphtho[1,8-bc]-1,5-thiazocin-4(5H)-one, or the hydrochloride salt thereof.

7. A compound in accordance with claim 3, wherein $R_1$ is 4-lower alkoxyphenyl and $R_2$ is hydroxy.

8. A compound in accordance with claim 7, wherein $R_1$ is 4-methoxyphenyl and $R_3$ and $R_4$ are independently lower alkyl and n is 2 to 3.

9. A compound in accordance with claim 8, (+)-cis-2,3-dihydro-5-[2-(dimethylamino)ethyl]-3-hydroxy-2-(4-methoxyphenyl)naphtho[1,8-bc]-1,5-thiazocin-4(5H)-one, or the hydrochloride salt thereof.

10. A compound in accordance with claim 2, wherein $R_1$ is 4-lower alkoxyphenyl and $R_2$ is selected from the group consisting of acetyloxy and propionyloxy.

11. A compound in accordance with claim 10, wherein $R_1$ is 4-methoxyphenyl, $R_2$ is acetyloxy, $R_3$ and $R_4$ are independently lower alkyl and n is 2 to 3.

12. A compound in accordance with claim 11, (+)-cis-3-(acetyloxy)-2,3-dihydro-5-[2-(dimethylamino)ethyl]-2-(4-methoxyphenyl)naphtho[1,8-bc]-1,5-thiazocin-4(5H)-one, or the hydrochloride salt thereof.

13. A compound in accordance with claim 3, wherein $R_1$ is 4-lower alkoxyphenyl and $R_2$ is selected from the group consisting of acetyloxy and propionyloxy.

14. A compound in accordance with claim 13, wherein $R_1$ is 4-methoxyphenyl, $R_2$ is acetyloxy, $R_3$ and $R_4$ are independently lower alkyl and n is 2 to 3.

15. A compound in accordance with claim 14, (+)-cis-3-(acetyloxy)-2,3-dihydro-5-[2-(dimethylamino)ethyl]-2-(4-methoxyphenyl)naphtho[1,8-bc]-1,5-thiazocin-4(5H)-one, or the (E)-2-butenedioate salt thereof.

16. A compound in accordance with claim 1, of the formula

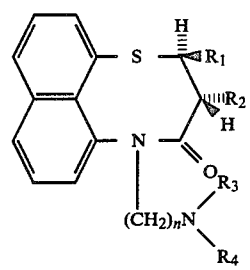

I<sup>III</sup> wherein $R_1$ is phenyl substituted with 1 to 3 lower alkoxy groups or 1 to 3 halogens; $R_2$ is hydroxy or lower alkanoyloxy; $R_3$ and $R_4$ are independently lower alkyl or together form a pyrrolidine or piperidine ring and n is 2 to 4;

an enantiomer or a racemate thereof or a pharmaceutically acceptable acid addition salt thereof.

17. A compound in accordance with claim 16, (±)-trans-3-(acetyloxy)-2,3-dihydro-5-[2-(dimethylamino)ethyl]-2-(4-methoxyphenyl)naphtho[1,8-bc]-1,5-thiazocin-4(5H)-one, or the hydrochloride salt thereof.

18. A compound of the formula

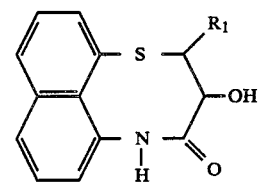

VI wherein $R_1$ is phenyl substituted with 1 to 3 lower alkoxy groups or 1 to 3 halogens.

19. A compound in accordance with claim 18, of the formula

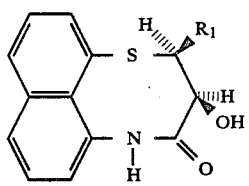

VI<sup>I</sup> wherein $R_1$ is phenyl substituted with 1 to 3 lower alkoxy groups or 1 to 3 halogens;

an enantiomer or a racemate thereof.

20. A compound in accordance with claim 19, wherein $R_1$ is 4-lower alkoxyphenyl.

21. A compound in accordance with claim 20, (±)-cis-2,3-dihydro-3-hydroxy-2-(4-methoxyphenyl)-naphtho[1,8-bc]-1,5-thiazocin-4(5H)-one or the hydrochloride salt.

22. A calcium channel blocking composition comprising an effective amount of a compound of the formula

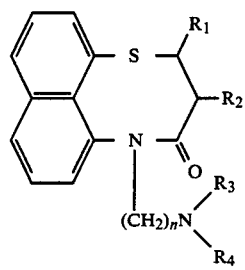

wherein R₁ is phenyl substituted with 1 to 3 lower alkoxy groups or 1 to 3 halogens; R₂ is hydroxy or lower alkanoyloxy; R₃ and R₄ are independently lower alkyl or together form a pyrrolidine or piperidine ring; n is 2 to 4;
or a pharmaceutically acceptable acid addition salt thereof, and a pharmaceutically inert carrier material.

23. A composition in accordance with claim 22, comprising an effective amount of a compound of the formula

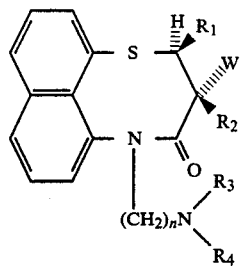

wherein R₁ is phenyl substituted with 1 to 3 lower alkoxy groups or 1 to 3 halogens; R₂ is hydroxy or lower alkanoyloxy; R₃ and R₄ are independently lower alkyl or together form a pyrrolidine or piperidine ring, and n is 2 to 4;
an enantiomer or a racemate thereof or a pharmaceutically acceptable acid addition salt thereof.

24. A composition in accordance with claim 23, comprising an effective amount of a compound of the formula

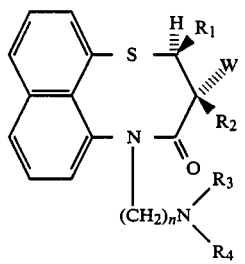

wherein R₁ is phenyl substituted with 1 to 3 lower alkoxy groups or 1 to 3 halogens; R₂ is hydroxy or lower alkanoyloxy; and R₃ and R₄ are independently lower alkyl or together form a pyrrolidine or piperidine ring, and n is 2 to 4;
or a pharmaceutically acceptable acid addition salt thereof.

25. A composition in accordance with claim 24, wherein R₁ is 4-lower alkoxyphenyl, R₂ is selected from the group consisting of acetyloxy and propionyloxy.

26. A composition in accordance with claim 25, wherein R₂ is acetyloxy, R₃ and R₄ are independently lower alkyl and n is 2 to 3.

27. A composition in accordance with claim 24, wherein the compound of formula I' is: (±)-cis-3-(acetyloxy)-2,3-dihydro-5-[2-(dimethylamino)ethyl]-2-(4-methoxyphenyl)naphtho[1,8-bc]-1,5-thiazocin-4(5H)-one, or the (E)-2-butenedioate salt thereof.

28. A method of inducing calcium channel blockage, which comprises administering to a warm-blooded animal in need of such treatment, an effective amount of a compound of the formula

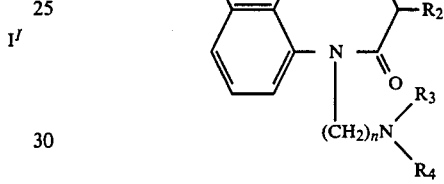

wherein R₁ is phenyl substituted with 1 to 3 lower alkoxy groups or 1 to 3 halogens; R₂ is hydroxy or lower alkanoyloxy; R₃ and R₄ are independently lower alkyl or together form a pyrrolidine or piperidine ring; n is 2 to 4;
or a pharmaceutically acceptable acid addition salt thereof.

29. A method in accordance with claim 28, which comprises administering a compound of the formula

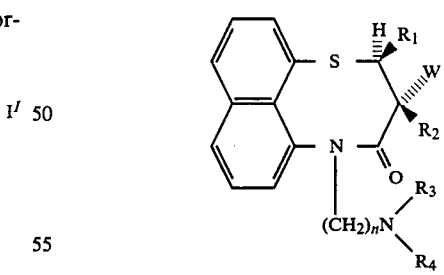

wherein R₁ is phenyl substituted with 1 to 3 lower alkoxy groups or 1 to 3 halogens; R₂ is hydroxy or lower alkanoyloxy; R₃ and R₄ are independently lower alkyl or together form a pyrrolidine or piperidine ring, and n is 2 to 4;
an enantiomer or a racemate thereof or a pharmaceutically acceptable acid addition salt thereof.

30. A method in accordance with claim 29, which comprises administering a compound of the formula

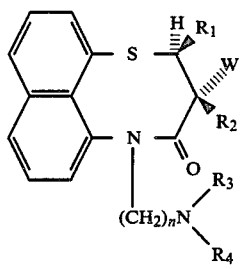

wherein $R_1$ is phenyl substituted with 1 to 3 lower alkoxy groups or 1 to 3 halogens; $R_2$ is hydroxy or lower alkanoyloxy; and $R_3$ and $R_4$ are independently lower alkyl or together form a pyrrolidine or piperidine ring, and n is 2 to 4;

or a pharmaceutically acceptable acid addition salt thereof.

31. A method in accordance with claim 30, wherein $R_1$ is 4-lower alkoxyphenyl and $R_2$ is selected from the group consisting of acetyloxy and propionyloxy.

32. A method in accordance with claim 31, wherein $R_2$ is acetyloxy, $R_3$ and $R_4$ are independently lower alkyl and n is 2 to 3.

33. A method in accordance with claim 32, wherein the compound of formula $I'$ is: (+)-cis-3-(acetyloxy)-2,3-dihydro-5-[2-(dimethylamino)ethyl]-2-(4-methoxyphenyl)naphtho[1,8-bc]-1,5-thiazocin-4(5H)-one, or the (E)-2-butenedioate salt thereof.

* * * * *

UNITED STATES PATENT AND TRADEMARK OFFICE
CERTIFICATE OF CORRECTION

PATENT NO. : 4,640,930
DATED : February 3, 1987
INVENTOR(S) : Erno Mohacsi and Jay P. O'Brien It is certified that error appears in the above-identified patent and that said Letters Patent is hereby corrected as shown below:

In column 23, claim 6, line 1, delete "(+)" and insert therefor -- ($\pm$) --.

In column 23, claim 12, line 2, delete "(+)" and insert therefor -- ($\pm$) --.

In column 26, claim 27, line 2, delete "($\pm$)" and insert therefor -- (+) --.

Signed and Sealed this

Seventh Day of June, 1988

Attest:

DONALD J. QUIGG

*Attesting Officer*     *Commissioner of Patents and Trademarks*